United States Patent [19]

Lester

[11] Patent Number: 5,055,107
[45] Date of Patent: Oct. 8, 1991

[54] SURGICAL INSTRUMENTS AND ASSEMBLIES

[75] Inventor: Graham G. Lester, Hythe, Kent, England

[73] Assignee: Smiths Industries Public Limited Company, London, England

[21] Appl. No.: 431,102

[22] Filed: Nov. 3, 1989

[30] Foreign Application Priority Data

Nov. 3, 1988 [GB] United Kingdom ............... 8825749

[51] Int. Cl.$^5$ .............................................. A61M 16/00
[52] U.S. Cl. ..................................... 604/51; 604/218; 604/272; 128/207.29
[58] Field of Search ................... 604/51, 272–274, 604/158, 164; 128/207.14, 207.29

[56] References Cited

U.S. PATENT DOCUMENTS

| | | | |
|---|---|---|---|
| 2,263,692 | 11/1941 | Everett | 604/273 |
| 3,841,334 | 10/1974 | Wolf | 128/207.29 |
| 3,886,946 | 6/1975 | Hyde | 128/207.29 |
| 3,916,903 | 11/1975 | Pozzi | 128/207.29 |
| 4,364,391 | 12/1982 | Toye | 128/207.29 |
| 4,520,810 | 6/1985 | Weiss | 128/207.29 |
| 4,677,978 | 7/1987 | Melker | 604/51 |

*Primary Examiner*—Stephen C. Pellegrino
*Assistant Examiner*—Ralph A. Lewis
*Attorney, Agent, or Firm*—Pollock, Vande Sande & Priddy

[57] ABSTRACT

A surgical instrument for use in forming a tracheostomy comprises a needle with a sharply pointed angled tip joined at its rear end to plastics hub. The length of the needle from the hub is greater than the thickness of neck tissue but less than the distance between the skin surface and the anterior wall of the trachea. The hub has a laterally extending face which has an area at least fifty times the cross sectional area of the needle. Two parallel walls have stepped edges which provide a gripping region for the hub, enabling it to be gripped between finger and thumb. A tapered recess in the hub receives the nose of a syringe which provides a loss of resistance device so that the plunger can be displaced along the barrel when the tip of the needle enters the trachea.

1 Claim, 3 Drawing Sheets

SURGICAL INSTRUMENTS AND ASSEMBLIES

BACKGROUND OF THE INVENTION

This invention relates to surgical instruments and assemblies.

The invention is more particularly concerned with surgical instruments for use in tracheostomy.

Where it is necessary to provide an emergency airway via a tracheostomy, or to enable a suction catheter to be introduced to the trachea or bronchial passages, this can be achieved by means of a relatively small diameter, uncuffed tracheostomy tube which does not hinder airflow to the patient s mouth and which enables the patient to cough and clear sputum normally.

The procedure is carried out by making a stab cut with a short-bladed scalpel through the neck into the trachea in the region of the cricothyroid membrane. The scalpel is then removed and the tracheostomy tube is inserted through the cut by means of an introducer with a tapered tip that projects from the patient end of the tube. Subsequently, the introducer is pulled rearwardly out of the machine end of the tube, leaving the tube in place to provide an air passage into the trachea.

In an alternative technique (The Seldinger technique), the cricothyroid membrane is pierced using a hollow needle after having first made an incision through the skin with a scalpel. A guide wire is then inserted through the needle into the trachea, the needle subsequently being withdrawn to leave the guide wire preserving access to the trachea. A dilator may then be fed over the guide wire to enlarge the opening into the trachea so that a tracheostomy tube can be introduced by sliding it over the dilator. Both the guide wire and the dilator are then withdrawn leaving the tube in position.

This technique has the advantage that the guide wire maintains the patency of the tracheostomy until the tracheostomy tube is inserted. There can otherwise be the tendency for the different layers of tissue in the neck to become displaced, especially if the patient should cough, making it difficult for the surgeon to insert the tracheostomy tube.

There is a disadvantage, however, with this technique in that it is possible for the needle to be pushed too far into the neck leading to possible damage to the posterior wall of the trachea. It is also possible that the needle could be pushed through the posterior wall of the trachea into the oesophagus; this could lead to the tracheostomy tube being inserted into the oesophagus rather the trachea.

BRIEF SUMMARY OF THE INVENTION

It is an object of the present invention to provide a surgical instrument for use in tracheostomy by which the above-mentioned disadvantage can be alleviated.

According to one aspect of the present invention there is provided a surgical instrument for use in forming a tracheostomy, the instrument comprising a hollow needle and a hub, the needle having a sharply pointed forward end and a rear end mounted in the hub, the length of needle projecting from the forward end of the hub being greater than the thickness of neck tissue between the skin surface and the anterior wall of the trachea but less than the distance between the skin surface and the posterior wall of the trachea, the hub having at its forward end a laterally extending face the area of which is at least fifty times the cross sectional area of the needle, and the hub having at its rear end a coupling that communicates with the bore of the needle and that is adapted to be coupled with a loss of resistance device, such that insertion of the instrument is limited by engagement of the face of the hub with the skin surface of the neck so that the forward end of the needle lies within the trachea without contacting the posterior wall of the trachea and such that entry of the forward end of the needle into the trachea can be detected by flow of fluid from the loss of resistance device through the needle The hub preferably includes a gripping region by which the instrument can be gripped between finger and thumb. The gripping region is preferably provided by two parallel walls with stepped edges and the forward end of the needle may be angled relative to the gripping region. The coupling at the rear end of the hub is preferably a tapered recess adapted to receive a cooperating tapered nose of the loss of resistance device. The area of the face may be at least 100 mm$^2$ and is preferably between 100-150 mm$^2$. The hub is preferably of a plastic material.

According to another aspect of the present invention there is provided a surgical instrument assembly comprising a surgical instrument according to the above one aspect of the invention and a loss of resistance device coupled to the surgical instrument.

The loss of resistance device preferably includes a syringe having a barrel coupled with the hub and a plunger that is movable along the barrel when the forward end of the needle lies within the trachea.

A surgical instrument and its method of use, in accordance with the present invention, will now be described, by way of example, with reference to the accompanying drawings.

DETAILED DESCRIPTION OF PREFERRED EMBODIMENT

Figure 1:
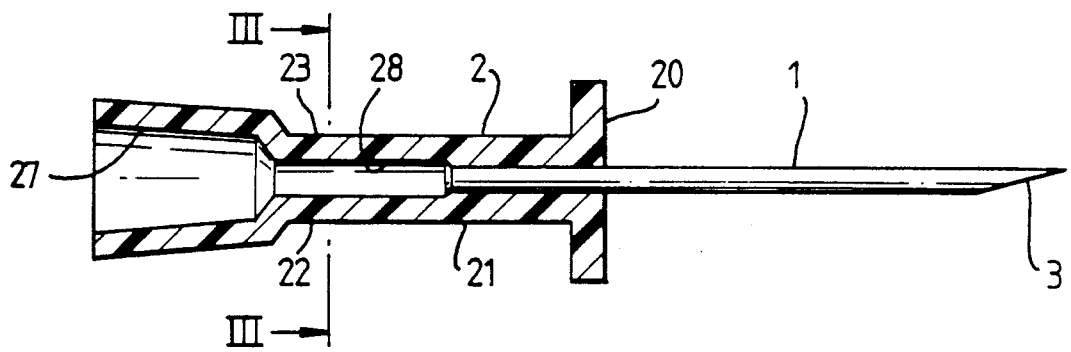
FIG. 1 is a partly sectional side elevation along the instrument.
Figure 2:
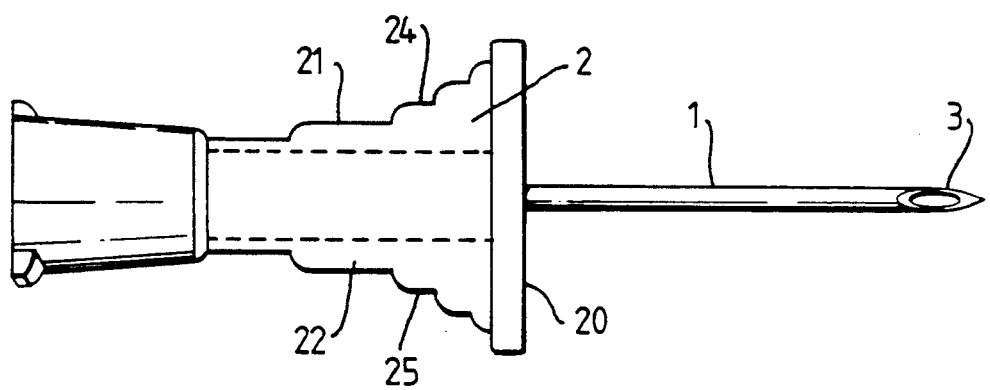
FIG. 2 is view from below of the instrument.
Figure 3:
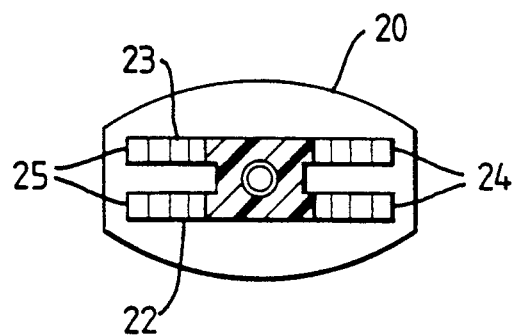
FIG. 3 is a transverse section along the line III—III of FIG. 1.

With reference first to FIGS. 1 to 3, the surgical instrument is in the form of a needle assembly comprising a hollow metal needle 1 joined at its rear end to a moulded plastics hub 2.

The needle 1 preferably is of 16 Gauge and is 17 mm long from the hub 2. At its forward end 3, the needle 1 is formed with a sharply pointed angled tip.

The hub 2 is approximately the same length as the needle 1. At its forward end, the hub 2 has a laterally extending flat face 20 which is preferably substantially rectangular in section but with its longer edges curved convexly. The face 20 is about 14 mm long and 10 mm wide at its widest point giving it a surface area of between 100-150 mm compared with the cross sectional area of the needle 1 which is about 2 mm$^2$.

The intermediate portion 21 of the hub, extending rearwardly from the face 20 provides a gripping region by which the hub can be gripped between finger and thumb. Two parallel walls 22 and 23 extend from the intermediate portion 21 and are stepped rearwardly to reduced width, the stepped edges 24 and 25 providing a non-slip gripping surface. The tip 3 of the needle 1 is angled away from the plane of the walls 22 so that the orientation of the needle tip can be determined from the orientation of the walls of the hub 2.

At its rear end, the hub 2 has a female Iuer-tapered coupling bore 27 of circular section which communicates with a smaller diameter bore 28 through the hub, which in turn communicates with the bore of the needle 1. The coupling bore 27 is conveniently about 4 mm in diameter at its rear end and is adapted to be coupled with a loss of resistance device 30 (FIG. 4).

Figure 4:
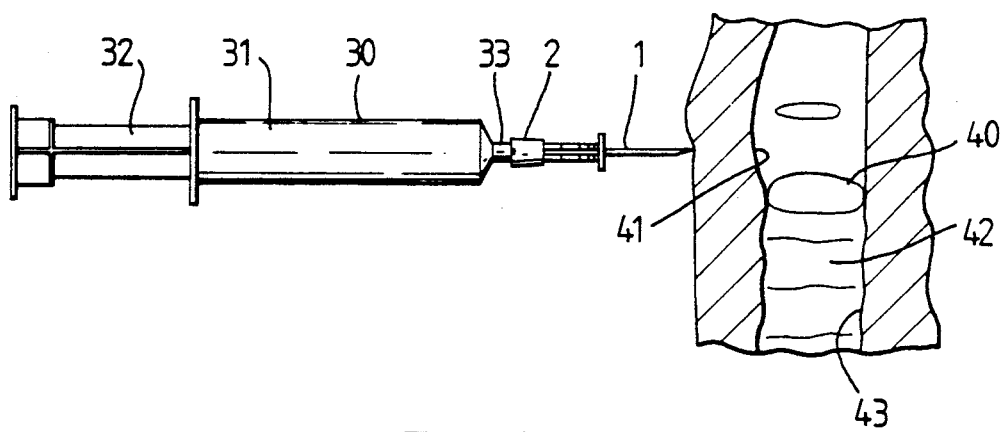
FIGS. 4 to 9 illustrate successive steps in use of the instrument.
Figure 5:
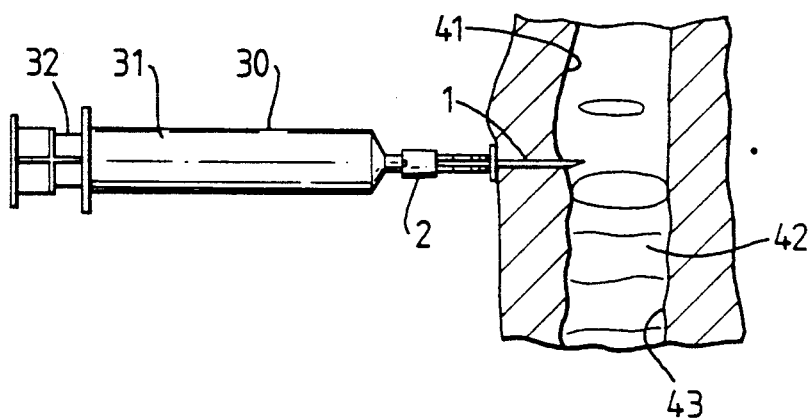

With reference now also to FIGS. 4 and 5, the loss of resistance device 30 is in the form of a syringe with a barrel 31 along which can be slid a plunger 32. The syringe has a luer-tapered nose 33 that can be coupled with the bore 27 in the hub 2.

Use of the instrument will now be described with reference to FIGS. 4 to 9. The loss of resistance device 30 is first coupled with the instrument hub 2 to form an instrument assembly. The plunger 32 is then pulled rearwardly towards the end of the barrel 31 and the tip 3 of the needle 1 is placed against the skin of the patient's neck in the region of the cricothyroid membrane 40, as shown in FIG. 4. The hub 2 is gripped between the finger and thumb of one hand with the hub oriented so that the face on the tip 3 of the needle is directed generally caudally. The other hand is used to apply a light forward pressure on the plunger 32. The instrument is pushed forwardly through the neck tissue and cricothyroid membrane 40 until the tip 3 of the needle 1 pierces the anterior wall 41 of the trachea 42, as shown in FIG. 5. In this position, air in the barrel 31 of the loss of resistance device 30 can escape through the instrument and out of its tip 3 into the trachea 42. This allows the plunger 32 to move forwardly within the barrel 31, indicating to the surgeon that the tip of the instrument has entered the trachea. The face 20 of hub 2 acts as a stop to prevent the instrument being inserted too far. The area of the face 20 is preferably at least about fifty times the cross-sectional area of the needle 1 so that there is no risk of the hub 2 entering the cut made by the needle. The length of the needle 1 projecting from the face 20 of the hub 2 is selected, according to the build of the patient (a different length of needle would be used for children), to be greater than the thick ness of neck tissue between the skin surface and the anterior wall 41 of the trachea 42 but less than the distance between the skin surface and the posterior wall 43 of the trachea.

Figure 6:
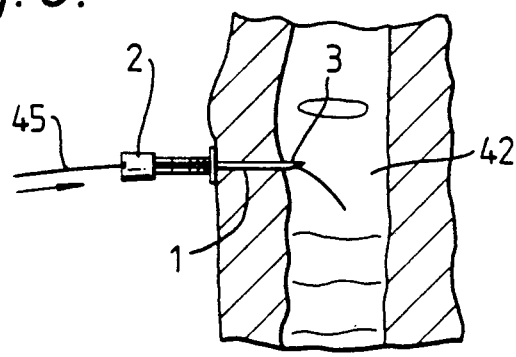

The loss of resistance device 30 is then uncoupled from the instrument, leaving the instrument in position in the trachea. A flexible guide wire 45, conveniently 500 mm in length, is pushed into the instrument far enough to project out of the forward end 3 of the needle 1, as shown in FIG. 6. The angled tip 3 of the needle helps ensure that the wire is directed caudally in the trachea, that is, towards the bronchial tract. In this respect, the needle could have a Tuohy tip which is bent to one side at its end.

Figure 7:
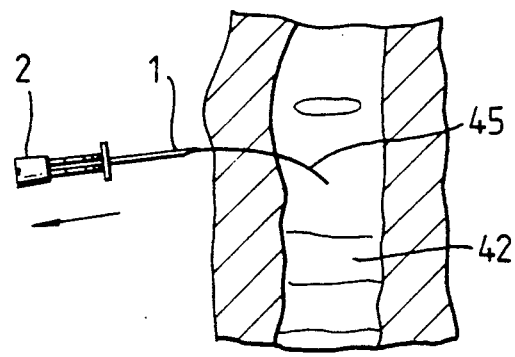

The instrument is then pulled rearwardly out of the trachea leaving the guide wire 45 in position, as shown in FIG. 7.

Figure 8:
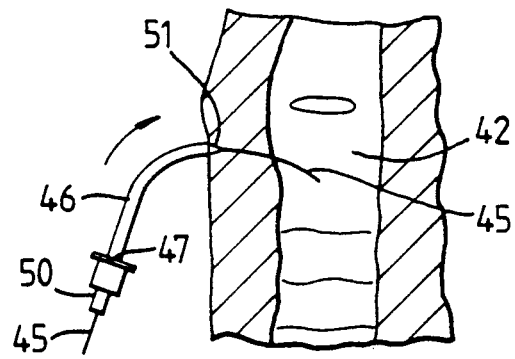

A small diameter uncuffed tracheostomy tube 46, typically with an internal diameter of 4 mm and of length about 130 mm, is slid onto a dilator 50 in the form of a curved rod with a pointed tip 51 which projects from the patient end of the tube 46. The dilator 50 has a central bore which receives the guide wire 45 so that the tube 46 and dilator can be slid along the guide wire, as shown in FIG. 8. The guide wire 45 maintains open the cut through the neck tissues and the pointed tip 51 of the dilator enlarges the cut as it is inserted, so that the tube 46 can be pushed into the trachea easily. The tube 46 has a flange 47 at its rear end which lies against the skin surface when it is fully inserted, with its forward end located in the trachea.

Figure 9:
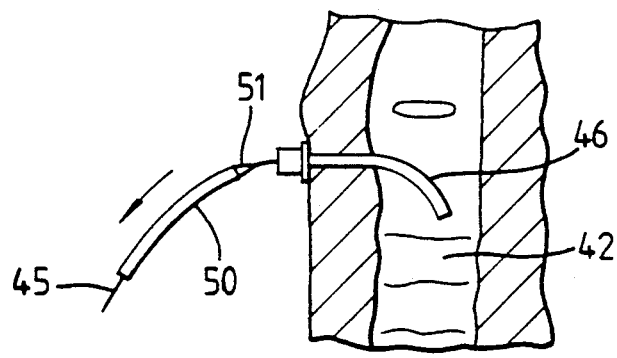

The dilator 50 and guide wire 45 are then pulled rearwardly out the trachea through the tube 46 which is left in position to provide an airway or access for suctioning as shown in FIG. 9.

The instrument of the present invention enables a tracheostomy opening to be performed rapidly with considerably reduced risk of damage to the trachea and of incorrect intubation.

What I claim is:

1. A method of forming a tracheostomy comprising the steps of: providing a surgical instrument comprising a hollow needle and a hub, the needle having a rear end mounted in the hub and a sharply pointed forward end that projects from a forward end of the hub, the length of needle projecting from the forward end of the hub being greater than the thickness of neck tissue between the skin surface and the anterior wall of the trachea but less than the distance between the skin surface and the posterior wall of the trachea, the hub having at its forward end a laterally extending face the area of said face being at least fifty times the cross sectional area of the needle, and the hub having at its rear end a coupling, said coupling communicating with the bore of the needle; providing a loss of resistance device, said loss of resistance device containing a fluid; coupling the loss of resistance device to the said coupling of the hub; pushing the forward end of the needle through the neck tissue of the patient; detecting flow of fluid from the loss of resistance device through the needle when the forward end of the needle lies within the trachea, insertion of the needle being limited by engagement of the face of the hub with the skin surface of the neck so that the forward end of the needle is prevented from contacting the posterior wall of the trachea; uncoupling the loss of resistance device from the instrument; inserting a flexible guide into the trachea directly through the needle; removing the needle to leave the guide in position; inserting a tracheostomy tube into the trachea along the guide; and subsequently removing the guide to leave the tracheostomy tube in position.

* * * * *